(12) United States Patent
Redmond et al.

(10) Patent No.: US 8,762,077 B2
(45) Date of Patent: Jun. 24, 2014

(54) DEVICE AND METHOD FOR MEASUREMENT OF CYCLING POWER OUTPUT

(75) Inventors: Barry Redmond, Dublin (IE); Ian Phillip Mellor, Dublin (IE)

(73) Assignee: Brim Brothers Limited, Dublin (IE)

( * ) Notice: Subject to any disclaimer, the term of this patent is extended or adjusted under 35 U.S.C. 154(b) by 504 days.

(21) Appl. No.: 12/996,903

(22) PCT Filed: Jun. 8, 2009

(86) PCT No.: PCT/EP2009/004095
§ 371 (c)(1),
(2), (4) Date: Dec. 8, 2010

(87) PCT Pub. No.: WO2010/000369
PCT Pub. Date: Jan. 7, 2010

(65) Prior Publication Data
US 2011/0087446 A1    Apr. 14, 2011

(30) Foreign Application Priority Data
Jun. 9, 2008 (IE) .................................. S2008/0470

(51) Int. Cl.
*G01L 1/00*     (2006.01)
*B62M 3/00*    (2006.01)

(52) U.S. Cl.
USPC .......................................... 702/44; 74/594.6

(58) Field of Classification Search
USPC ...................... 702/44, 33, 41–43, 81, 84, 127, 702/138–139, 141–142, 145, 148, 150–154, 702/182–183, 189; 33/1 N, 1 PT, 281–282, 33/285; 73/1.08–1.09, 1.37, 1.75, 379.01, 73/379.07, 488, 493, 510–511, 862.08, 73/862.381, 862.391; 74/594.1, 594.4, 74/594.6

See application file for complete search history.

(56) References Cited

U.S. PATENT DOCUMENTS

| | | | |
|---|---|---|---|
| 7,257,468 B1 * | 8/2007 | Costa et al. ....................... 701/1 |
| 8,122,773 B2 * | 2/2012 | Wyatt et al. ..................... 73/818 |
| 2004/0225467 A1 | 11/2004 | Vock et al. .................... 702/142 |
| 2006/0248965 A1 | 11/2006 | Wyatt et al. .............. 73/862.391 |
| 2007/0245835 A1 | 10/2007 | Hauschildt ............... 73/862.391 |

OTHER PUBLICATIONS

Corazza et al., Continuous Monitoring of the Physical Work and Power in Cycling, Sep. 9-13, 2002, 12th International Conference on Mechanics in Medicine and Biology, 10 pp.*

* cited by examiner

*Primary Examiner* — Toan Le
(74) *Attorney, Agent, or Firm* — Occhiuti & Rohlicek LLP

(57) ABSTRACT

The invention provides a measurement device and method for measuring a cyclist's power output, in response to an external force provided by said cyclist applied to a bicycle, including a force sensor (13), characterised in that said force sensor is embedded in a bicycle cleat (11) bolted to the shoe (10). The invention further provides an accelerometer (14) for measuring a cyclist's power output. The inventive device and method provides a number of advantages over prior art solutions. The device of the invention means that the installation does not need any part of the bicycle to be replaced. The present invention does not restrict the type of components that may be used on the bicycle. Because the sensors are embedded in the cleat it is very simple to move the system to another bicycle. The invention also allows for detailed analysis of pedalling style, leading to improvements in efficiency.

17 Claims, 16 Drawing Sheets

DEVICE AND METHOD FOR MEASUREMENT OF CYCLING POWER OUTPUT

CROSS-REFERENCE TO RELATED APPLICATIONS

This application is the National Stage of International Application No. PCT/EP2009/004095, filed on Jun. 8, 2009, which claims the priority date of Ireland Application No. S2008/0470, filed on Jun. 9, 2008 the contents of both being hereby incorporated by reference in their entirety.

FIELD OF THE INVENTION

The invention relates to the continuous measurement of a cyclist's power output, and in particular by utilising sensors and appropriate electronics in conjunction with a bicycle.

BACKGROUND TO THE INVENTION

Continuous measurement of a cyclist's power output is important because it adds greatly to the information available for analysing training activities and competition performance. This is particularly relevant for high performance competitors. Achieving higher power output for longer periods is one of the most important ways in which a competitive cyclist can improve their performance. Cyclists' training programmes are frequently based on maintaining specified power output for specified durations. Monitoring of power output during competition allows a cyclist to adjust their effort to make best use of their energy. If power output is recorded during an activity, it can be examined and analysed afterwards to identify areas needing improvement and to help form future training programmes.

There is a number of existing prior art systems for measuring a cyclist's power output on a bicycle when a bicycle is moving. Typically a prior art system displays instantaneous power to the cyclist on a unit mounted on the handlebars, and provides a facility to record the variation in power over a period of a few hours and download the information onto a computer later for analysis. There are four principal commercial systems available, each using different sensing techniques. Unlike measuring speed or pedalling cadence or heart rate, which can be done by observing and counting some activity without interfering with it, measuring force or power is very difficult to do without inserting a sensing element as a part of the power transmission path. The four existing power measurement systems each insert a sensor at a different point in the power transmission path between the cyclist's feet and the tyre contact with the road, as described below.

The first known system is "PowerTap" which uses strain gauges embedded in the hub of the rear wheel of the bicycle. This measures the mechanical strain as the rotational power is transferred from the rear gear cogs through the hub mechanism into the wheel itself. This system requires the use of a special rear wheel, built with the PowerTap hub at its centre. The use of a special wheel is a serious disadvantage, as competitive cyclists change wheels frequently. This system is described in U.S. Pat. No. 6,418,797.

A second system known as "SRM" uses strain gauges embedded in the right hand pedal crank that drives the chain. This measures the strain as the rotational power is transferred from the crank to the large gear ring driving the chain. This system requires the use of a special crank set containing the measurement sensors. The operation of this system is further described in http://www.srm.de/englisch/index.html.

The third system known in the industry as "Ergomo" uses strain gauges embedded in the axle that joins the two pedal cranks together through the bottom of the bicycle frame. It measures the strain as the axle twists slightly when the pedals are pressed by the cyclist. It measures the power from the left pedal only, and assumes that the power from the right pedal is exactly the same (which is hardly ever the case in practice). This system requires the use of a special axle and bearing assembly between the cranks. The Ergomo system is described in U.S. Pat. No. 6,356,847.

The "Polar" system is the only existing power measurement system that does not require a part of the bicycle to be replaced. It works by using sensors to monitor the tension in the chain, as disclosed in U.S. Pat. No. 6,356,848 The sensors are fitted close to the chain to monitor its speed and vibration. Installation requires measurement of the length and weight of the chain. It has a reputation for being difficult to install and calibrate, and for being less reliable than other systems.

All of the systems described above share a number of disadvantages. For example, installation of all these systems requires significant time, effort and expertise, and most cyclists will have to pay their local bike shop to do the job. The requirement to fit sensors and replacement parts to the bicycle means that the systems cannot be moved to another bicycle without significant time and effort. Most competitive cyclists own a number of bicycles, for different types of event, so this is a serious limitation. All but the Polar system require the use of special replacement parts, which limits the freedom of the cyclist to choose the parts that they want to use. None of the systems can accurately measure the power output from each foot, although they can infer it to some extent by relating variations in overall power output to the position of the pedals. This is not an accurate method, because it must assume that all the measured power comes from the foot on the downward stroke. It cannot take into account the power that the foot on the upward stroke may be adding (by pulling up) or subtracting (by pressing down). None of the above systems can measure "wasted" power, where a cyclist presses down on a pedal while it is on the up stroke. None of the above systems can measure how evenly and efficiently the cyclist is pressing on the pedal on the downward stroke.

PCT patent publication number WO2006121714 "Systems and methods of power output measurement" attempts to overcome the above mentioned problems. This PCT publication discloses a system for measuring the power output of a cyclist by placing sensors underneath the cyclist's shoe. A number of problems associated with this system include fitting the sensor between the cleat and shoe increases the distance from the cyclist's foot to the axle of the pedal, which reduces cycling efficiency. Variations in the force used to screw the cleat to the shoe will cause unknown force on the sensor, leading to an unknown "zero" point and calibration errors. The system takes no account of the need to measure the pedalling rate ("cadence") and the angular position of the crank at each instant. Rotational power at any instant cannot be calculated without knowing the applied force, the speed of rotation and the angular position of the crank thus leading to inaccurate data. The sensor and its connector are under the shoe, and therefore are exposed to damage during use.

PCT patent publication number WO2008/058164, assigned to Quarq, discloses a system that operates very similarly to the SRM system (described above). The system requires use of a special crank set with strain gauges embedded in the right hand side of the crank. The system also discloses the use of an accelerometer for certain measurements, when mounted on the crank assembly and requires a magnet on the bicycle. The system disclosed in Quarq is complex to implement as there is different crank sets for different manufacturers.

US patent publication number US 20070245835, assigned to Microsport, describes a system using measurements from a flexible force sensor inside a cyclist's shoe. The system measures only the compression force normal to the plane of the shoe and pedal. The system does not include any means to measure the direction of the force being applied through the pedals to the cranks, and uses pre-calculated estimates of direction based on assumptions of standard cycling styles.

There is therefore a need to provide a device, system and method to overcome the above mentioned problems. An object of the invention is to provide a device and method to measure, display and record the power output of a cyclist accurately and more effectively than current solutions on the market.

SUMMARY OF THE INVENTION

According to the present invention there is provided, as set out in the appended claims, a measurement device for measuring a cyclist's power output, in response to an external force provided by said cyclist applied to a bicycle, comprising a force sensor, characterised in that said force sensor is embedded in a bicycle cleat.

Heretofore, no measurement device for measuring the power output of a cyclist has been embedded in a bicycle cleat. The invention provides a constant measurement solution of the power output of a cyclist, with a number of advantages over existing systems that have a number of problems already mentioned in the Background of the Invention. For example the inventive device means that the installation does not need any part of the bicycle to be replaced. The present invention does not restrict the type of components that may be used on the bicycle. Because the sensors are embedded in the cleat it is very simple to move the system to another bicycle. The invention allows for detailed analysis of pedalling style, leading to improvements in efficiency.

In another embodiment the measurement device is provided with an accelerometer. Heretofore, accelerometers have not been used for the measurement of power output of a cyclist. In a preferred embodiment the present invention found that positioning or embedding an accelerometer in a bicycle cleat allows for accurate measurements that were not measured previously, to aid in increasing the performance of a cyclist.

In another embodiment the accelerometer can be mounted anywhere in the vicinity of the rotating mechanism, said accelerometer comprises means for measuring cadence or crank position or pedal tilt. It will be appreciated that the invention makes use of measurement of the foot angle, such that a vector is obtained to determine where the pressure is coming from to calculate torque from the foot force. The foot angle provides important data from a biomechanical point of view for the cyclist.

In another embodiment of the present invention there is provided a measurement device for measuring a cyclist's power output, in response to an external force provided by said cyclist applied to a bicycle, comprising an accelerometer. It will be appreciated that positioning the accelerometer anywhere in the vicinity of the pedal, for example either mounted on the pedal or in the bicycle cleat or bicyclist shoe allows for accurate measurements to measure the cyclist's power output. Suitably the accelerometer can be mounted on the cleats and/or legs and/or feet and/or shoes and/or pedals for measuring cadence or crank position or pedal tilt.

Optionally, the embedded force sensor comprises a first sensor positioned on the inner edge of said cleat and a second sensor positioned on the outer edge of said cleat. In a further embodiment the force sensor comprises a third sensor positioned on the centre of the cleat.

Ideally, the force sensor comprises means for measuring the compression force applied to said bicycle cleat. It will be appreciated that a single sensor can measure both the compression and tension forces.

Suitably, the force sensor comprises means for measuring the shear force applied to said cleat.

Ideally, the accelerometer comprises means to measure pedalling cadence. The accelerometer comprises means to detect the true top of a crank revolution. Suitably, the accelerometer comprises means to detect the true bottom of a crank revolution.

Ideally the accelerometer comprises means to measure the angular position of the crank and means to measure forward/backward tilt of the pedal.

Compared to other systems measuring force in the shoe or pedal assembly, the present invention measures crank angle and force direction more accurately, thus providing a more accurate power figure. Use of the force sensors in combination with an accelerometer provides measurement of forces applied by each or either foot at all points in a revolution, allowing identification of "wasted" power applied downwards during the up stroke.

The invention provides measurement of forces at more than one point under each foot, allowing identification of inefficiencies caused by leaning to the left or the right on the pedal. Accurate measurement of the forward/backward tilt of the cyclist's foot and shoe, provides extra information about pedalling style. The invention provides measurement of the direction of the force applied to the pedal, allowing identification of inefficiencies due to pushing in the wrong direction. The invention can provide measurement of the cycling cadence without requiring sensors or components to be attached to the bicycle.

In a further embodiment of the present invention there is provided a method of measuring a cyclist's power output, in response to an external force provided by said cyclist applied to a bicycle, comprising the step of using a force sensor embedded in a bicycle cleat to measure the force applied. Ideally the invention provides the additional step of using an accelerometer.

There is also provided a computer program comprising program instructions for causing a computer program to carry out the above measurements which may be embodied on a record medium, carrier signal or read-only memory.

BRIEF DESCRIPTION OF THE DRAWINGS

The invention will be more clearly understood from the following description of an embodiment thereof, given by way of example only, with reference to the accompanying drawings, in which:—

DETAILED DESCRIPTION OF THE DRAWINGS

Figure 1:
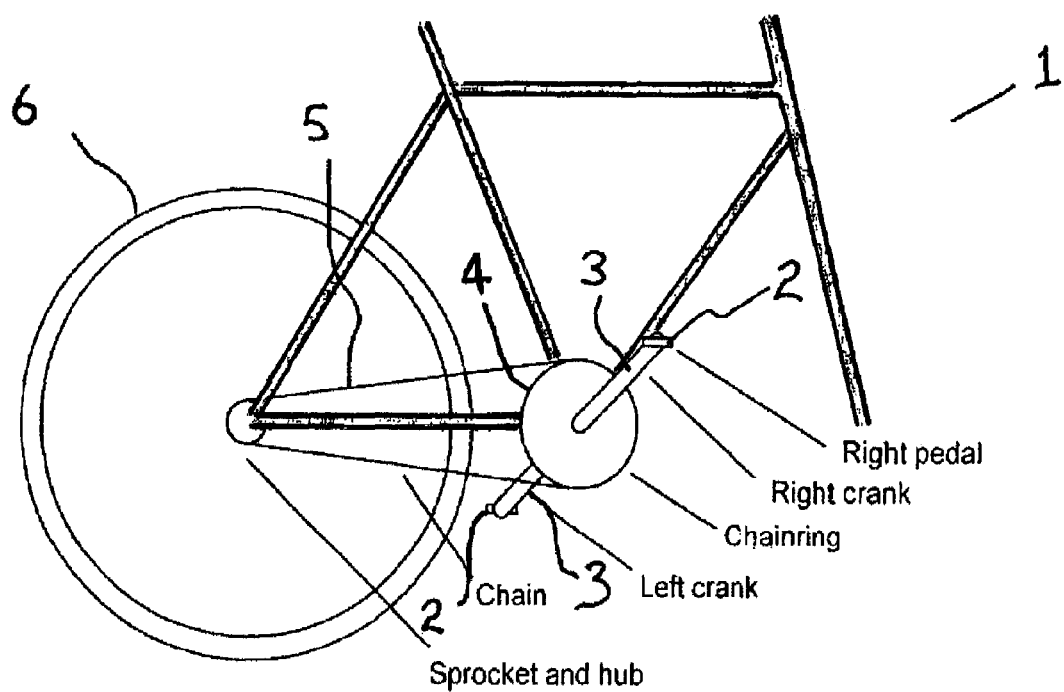
FIG. 1 illustrates a typical prior art bicycle power train, showing the components used to transmit power from pedal through cranks, chain, sprocket, hub, and rear wheel.

FIG. 1 shows energy exerted on the pedals of a bicycle that passes through a sequence of mechanical components (the "power train") before it drives the rear tyre against the road surface, illustrated generally by the reference numeral 1. A cyclist presses down on pedals 2 attached to cranks 3, one on each side. The cranks 3 rotate on an axle through the bottom of the bicycle frame (known as the "bottom bracket") and drive a chain ring, 4 which drives the chain 5. The chain 5 drives a gear (usually selected from one of several) attached to the hub of a back wheel 6. The hub of the back wheel 6 rotates on its axle, transmitting torque out through the spokes to rotate the whole wheel and drive the tyre against the road surface.

Figure 2:
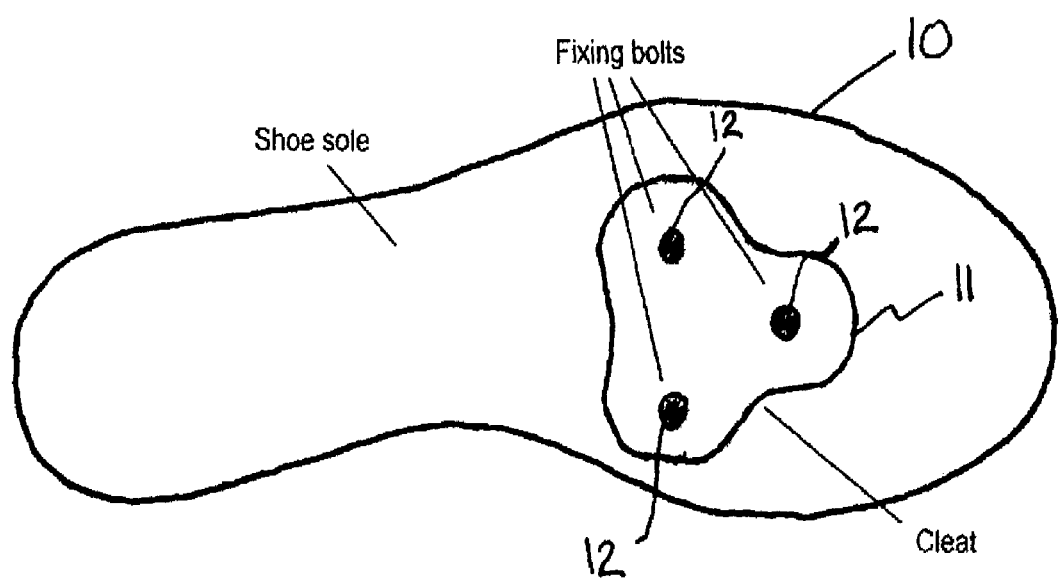
FIG. 2 shows a bottom view of a typical cycling shoe and bicycle cleat.
Figure 3:
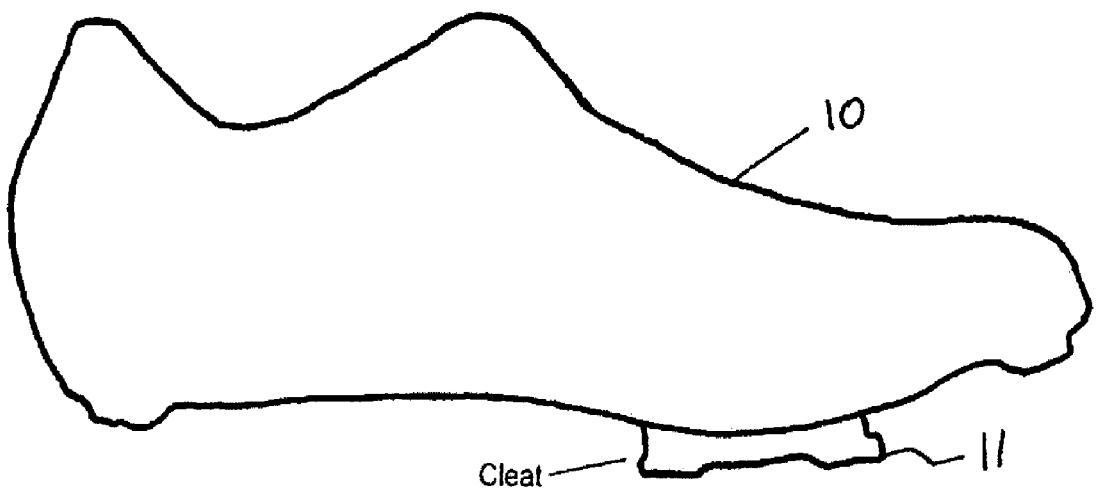
FIG. 3 shows a side view of a typical cycling shoe and bicycle cleat.

Referring to FIGS. 2 and 3, typically for a competition bicycle the cyclist's shoes, indicated generally by the reference numeral 10, are locked onto the pedals 2 by quick-release cleats 11. The cleat 11 is normally made of a hard plastic, and can be tightly bolted to the bottom of the shoe 10. The pedals 2 are specially shaped to accept the cleats and are spring loaded to hold them tightly. When clipped in, the only way to remove the shoe 10 and cleat 11 from the pedal 2 is to rotate them sideways. This arrangement ensures the cyclist's foot does not slip off the pedal 2, and also allows a cyclist to pull up on the shoe to impart force on the upward stroke. In use, cleats 11 become worn and typically have to be replaced after six months to a year of use. There are a number of different cleat and pedal designs available on the market, and they are generally not compatible with each other. In the context of the present invention the term 'embedded' can mean that the sensor 13 is partially or wholly within the cleat 11.

Figure 4:
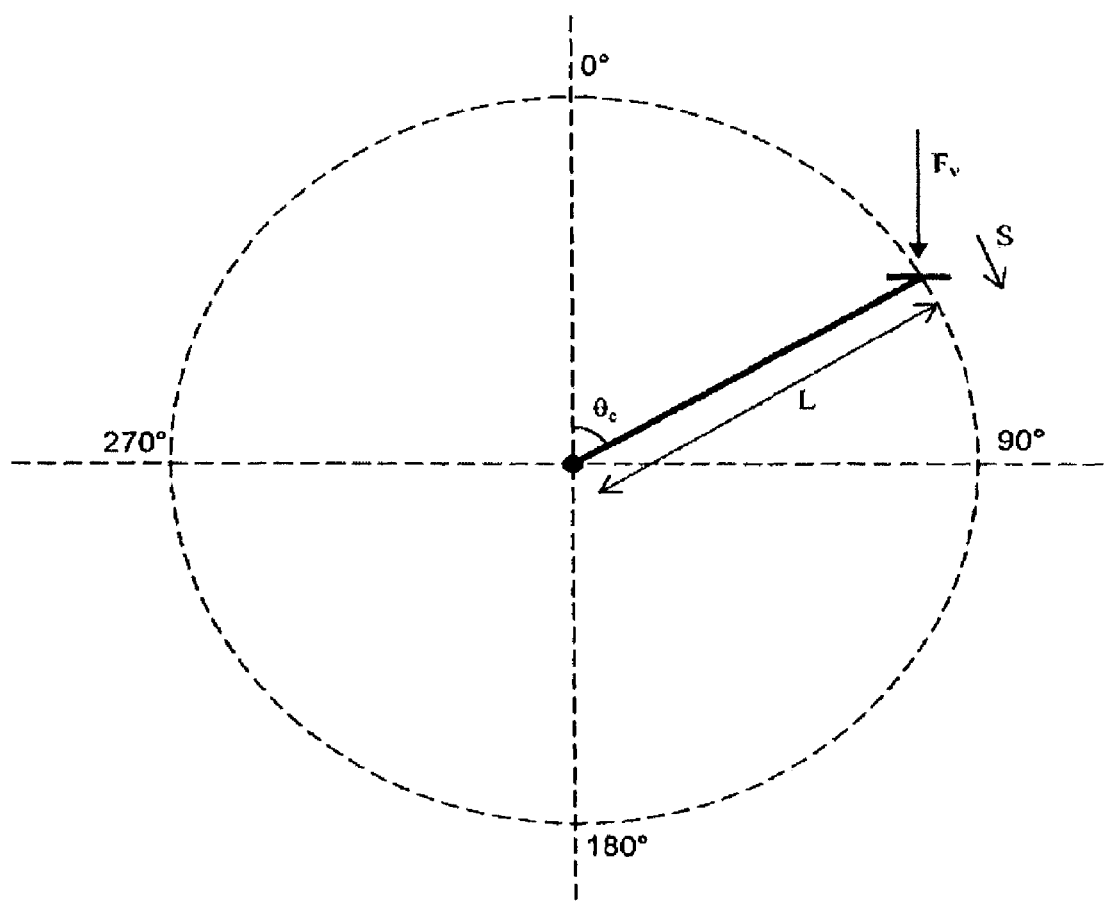
FIG. 4 illustrates required values to calculate the power by using the vertical component $F_v$ of the force applied to a pedal and crank.
Figure 5:
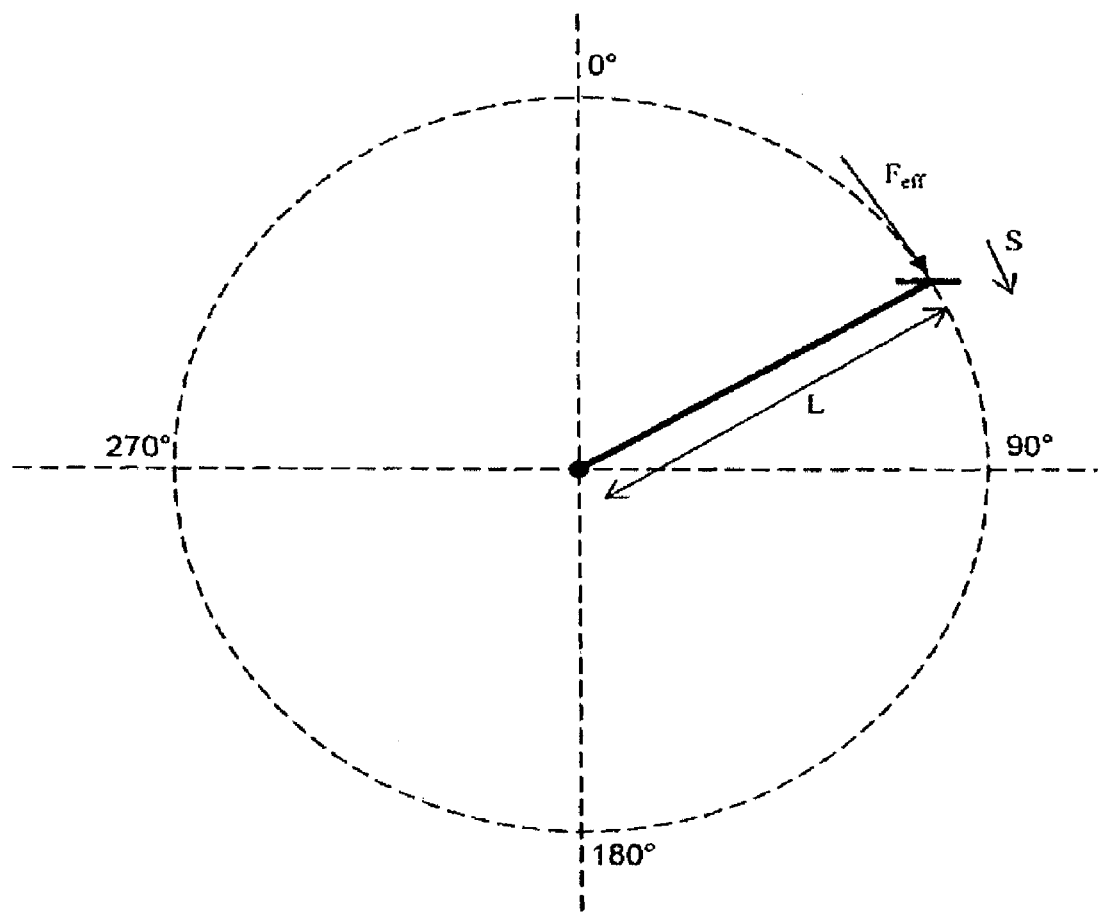
FIG. 5 illustrates known values required to calculate the power by using the effective component $F_{eff}$ of the force applied to a pedal and crank.

Referring to FIGS. 4 and 5 the process for converting the measured force imparted by a cyclist on a pedal into an accurate power value depends on where in the power train the force was measured. Force only produces power when work is done (i.e. something moves), so calculating power depends on what is moved and at what rate. The force applied to the pedals causes the cranks and pedals to rotate, so the movement is rotational.

The equation to calculate rotational power at one instant is:

$$P = T*S$$

'P' is the calculated power, in Watts.
'T' is the torque, in Newton-metres.
'S' is the speed of rotation, in radians/second.

The torque T due to a force applied vertically via a crank as shown in FIG. 4 is:

$$T = F_v * L * \sin(\theta_c)$$

'$F_v$' is the vertical component of the applied force, in Newtons.
'L' is the length of the crank from its centre of rotation to the pedal, in metres.
'$\theta_c$' is the angle of the crank forwards from the top of its revolution.

Alternatively, if the force component $F_{eff}$ acting perpendicular to the end of the crank in the direction of rotation, as shown in FIG. 5, is known at an instant, then the equation for torque T at that instant is:

$$T = F_{eff} * L$$

'$F_{eff}$' is the effective component of the applied force, perpendicular to the crank, in Newtons.
'L' is the length of the crank from its centre of rotation to the pedal, in metres.

From these variables it can be seen that calculating power for each instant requires measurement of three variable quantities at that instant: the applied force, the rotational speed (cadence), and the crank angle. It also requires knowledge of the length of the crank, but this is fixed and known for any bicycle, and can be entered into the system by the user.

By repeatedly measuring the three variable quantities of force, cadence and angle at known regular intervals during each revolution of the cranks the cyclist's torque and power output at each of those instants may be calculated, and the average torque and power over a crank revolution or over a specified period of time can be derived and displayed to the cyclist. The measurements taken at regular intervals are referred to as samples, and the time interval between samples is referred to as the sampling interval.

Figure 6:
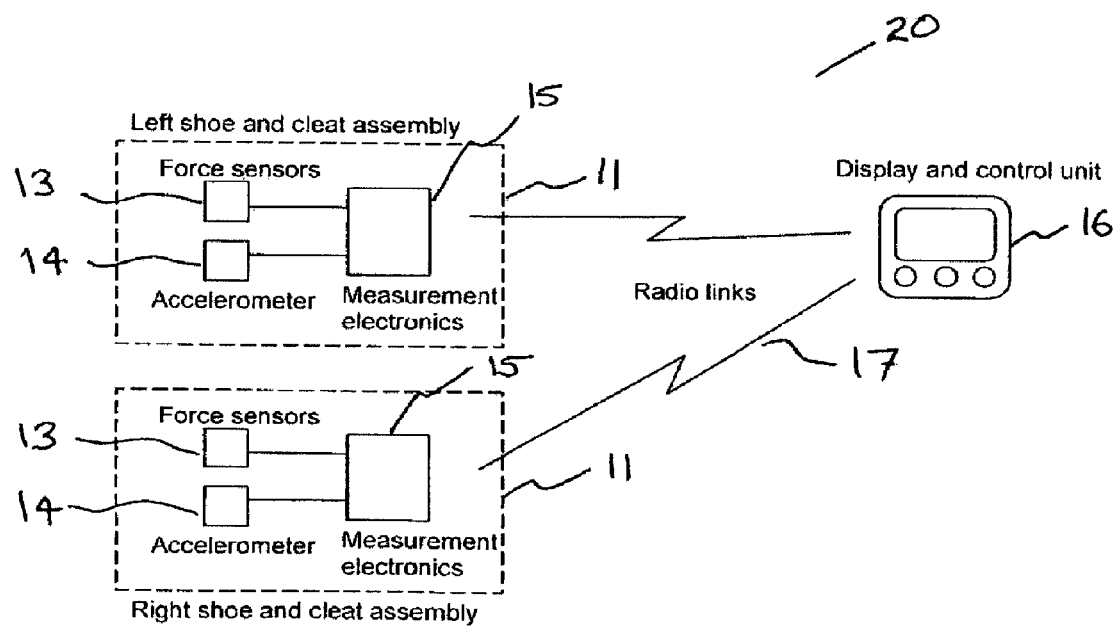
FIG. 6 illustrates of the overall system architecture of the present invention.

Referring to FIG. 6 there is illustrated a system to implement the present invention indicated generally by the reference numeral 20. A pair of cleats 11 are indicated by the dotted line and are in communication with a control and display unit 16, for example over a radio link 17. Each cleat 11 comprises of one or more force sensor(s) 13, an accelerometer 14 and related measurement electronics 15 embedded in each cleat 11 and attached to each of the two shoes. The display and control unit 16, usually battery powered, can be attached to any convenient place such as the handlebar of the bicycle or the wrist of the cyclist. The connection between the sensors and electronics in the cleat and the sensors and electronics elsewhere in or on the shoe may be by wired cables on or integrated into the shoe, or may be by another wireless link such as radio or electromagnetic induction. It will be appreciated that the preferred embodiment of the present invention is that the sensors 13, 14 are wholly embedded in the cleat 11, for example as shown in the side view of FIG. 8 such that the sensors are integrally moulded with the cleat during manufacture. In addition the measurement electronics 15 can be positioned in the heel of a cyclist shoe. It will be appreciated that the sensors 13 can be partially or wholly embedded in the cleat 11. It is envisaged that the sensors 13 can be replaceable in the cleat depending on the application required.

In a preferred embodiment the communication between the electronics embedded in the cleat and the display and control unit is by a radio link 17. Each cleat 11 uses the radio to transmit a set of measurement data at one or more fixed points on each revolution of the cranks. In operation each cleat 11 transmits its data in a short burst when the crank reaches a fixed point on its revolution, such as the top or the bottom. Because the two cranks are 180 degrees away from each other this ensures that the transmissions from each cleat 11 assembly will never interfere with each other. Each burst of data contains a set of samples or measurements taken at regular intervals during the crank revolution, and may include force, cadence, crank angle and accelerometer information. Each sample has an associated timestamp, which may be explicit or implicit, to specify its time relationship to the other samples in the set and to other sets of samples. The electronics in the cleat 11 may include processing of the data before it is transmitted to the control unit 16.

Figure 7:
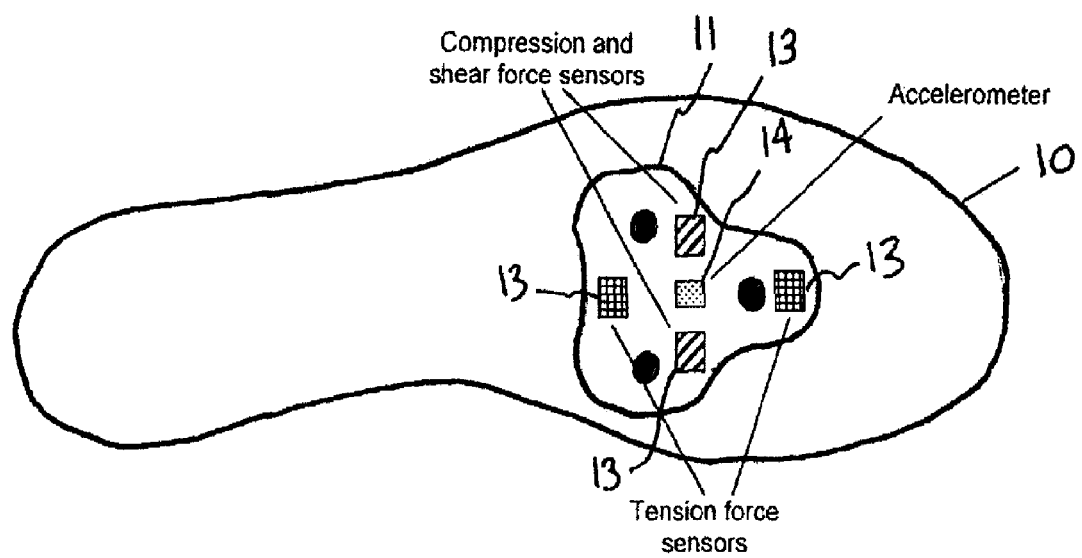
FIG. 7 illustrates a bottom view of the force sensors and accelerometer embedded in the cleat according to one aspect of the invention.
Figure 8:
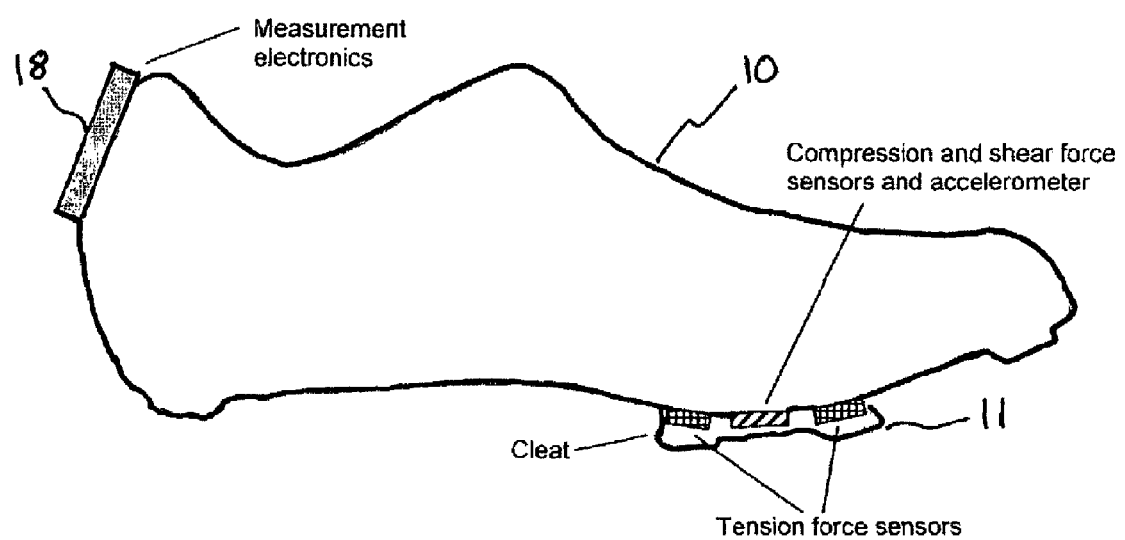
FIG. 8 illustrates a side view of FIG. 7 of the force sensors and accelerometer embedded in the cleat.

Referring to FIGS. 7 and 8 one preferred aspect of the invention is described where force is measured by embedding sensors in the cleats in operation. As the cyclist applies force through their shoes and cleats onto the pedals the sensors generate an electrical output representing the instantaneous force being applied. The sensors are embedded and positioned in the cleats 11 so that a known fraction of the total applied force is measured by them, and so that force is sensed at a number of points, including both the left and right side of each cleat. The positioning of the force sensors 13 is very advantageous as more accurate force measurements are obtained. The sensors can be any force measurement sensors of appropriate size and measurement range. It will be appreciated that the positioning of the sensors depends on the shape or design of the cleat. Ideally the sensors 13 accurately measure the force applied by positioning a sensor in the centre line of the shaft. It is envisaged that the invention can provide three force sensors to provide accurate measurement of force applied.

The cleats 11 include separate force sensors positioned to measure any upward tension (pull up) force, in addition to those positioned to measure the downward compression (press down) force. Depending on the pedalling style of the cyclist, pull up forces may occur on the upward pedal stroke, contributing to the total power applied to the pedals. Detection and measurement of any pull up force allows a more complete measurement of the applied power, and a more detailed analysis of the cyclist's pedalling style. Separate sensors positioned in different parts of the cleat are needed for compression and tension forces because typically these two forces pass through different parts of the cleat.

Figure 9:
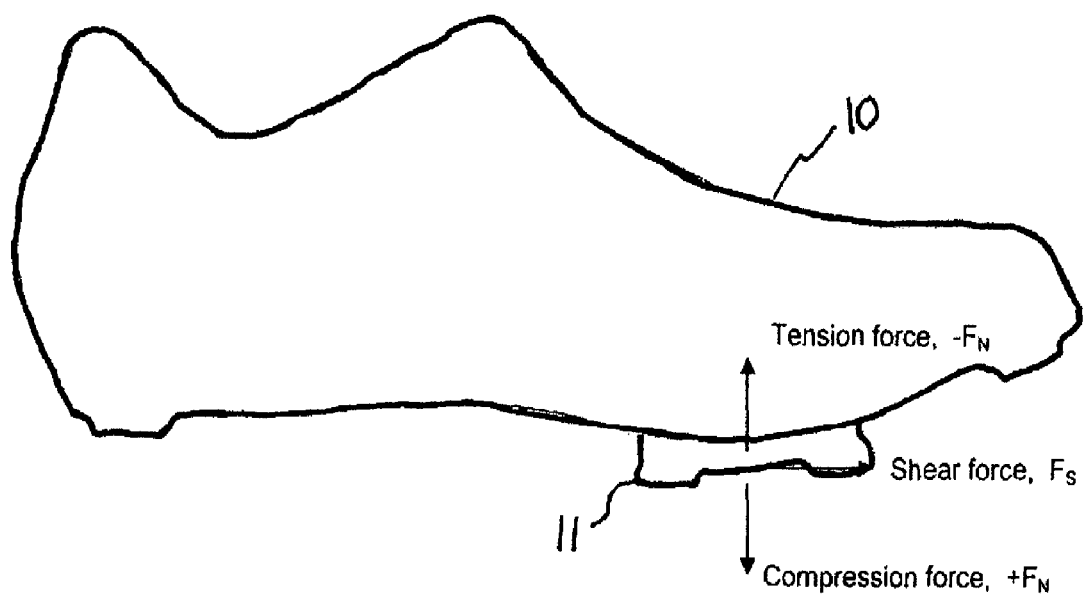
FIG. 9 illustrates the directions of the compression, tension and shear forces at the cleat.

FIG. 9 shows another aspect of the present invention cleat where sensors 13 are positioned to measure shear force between the cleat and the pedal, at right angles to the force measured by the compression and tension force sensors. Combining measurement information from the shear, compression and tension force sensors allows calculation of the direction of the total force applied to the cleat 11.

It will be appreciated that the force measurements from the sensors in each shoe are combined to produce a value for normal force $F_N$ downwards from the shoe through the cleat to the pedal and a value for shear force $F_S$ parallel to the surfaces of the cleat and pedal. These values must be multiplied by known calibration constants because only known fractions of the total force are typically measured by the sensors 13.

Figure 10:
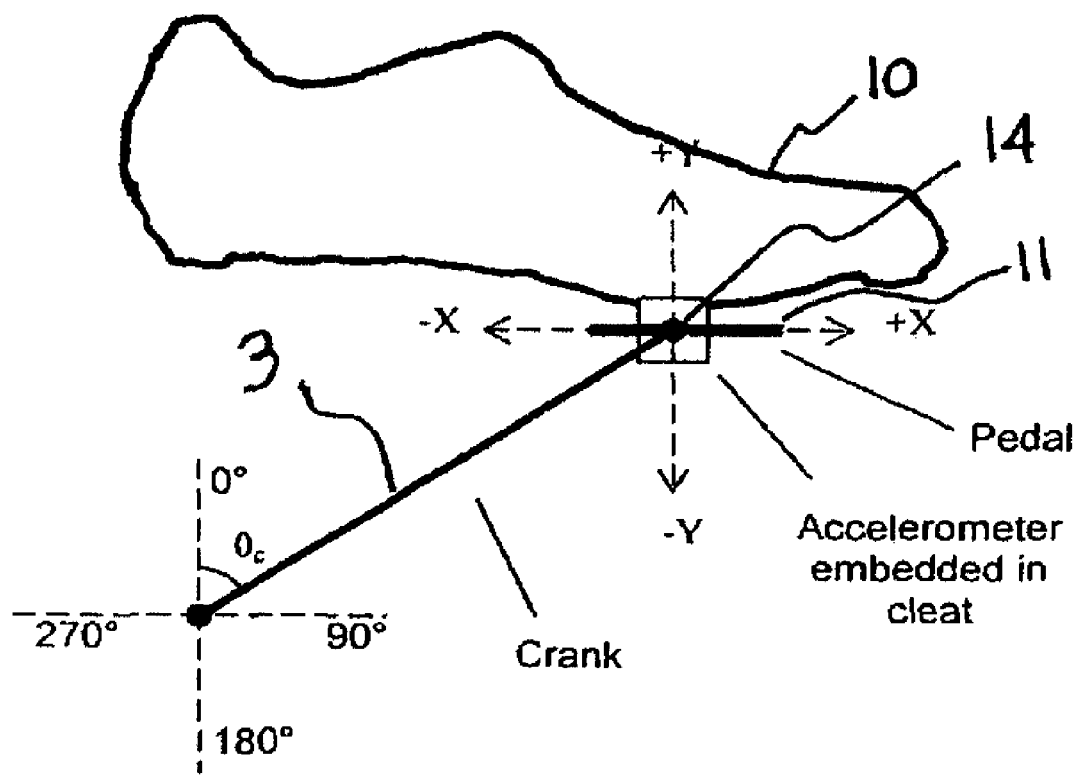
FIG. 10 illustrates X and Y axes of an accelerometer with respect to the shoe, cleat, pedal and crank.

In a further aspect of the present invention, the invention provides for the accurate measurement of cadence and crank angle by using one or more accelerometers 14 attached to or embedded in the cleat 11, illustrated in FIG. 10. The accelerometer 14 can measure acceleration in at least two axes, perpendicular to each other, and typically this is done using a single accelerometer device that measures in two or more axes. Such accelerometers 14 are commercially available and usually provide one electrical output signal for each axis. The accelerometer is mounted so that both axes are in the same plane as the plane of rotation of the cranks. As illustrated in FIG. 10 typically one axis is vertical (the Y axis) and the other is horizontal (the X axis) from front to back of the bicycle when the cleat 11 and shoe 10 are horizontal, although any orientation of the axes in the plane of rotation of the cranks may be used.

Figure 11:
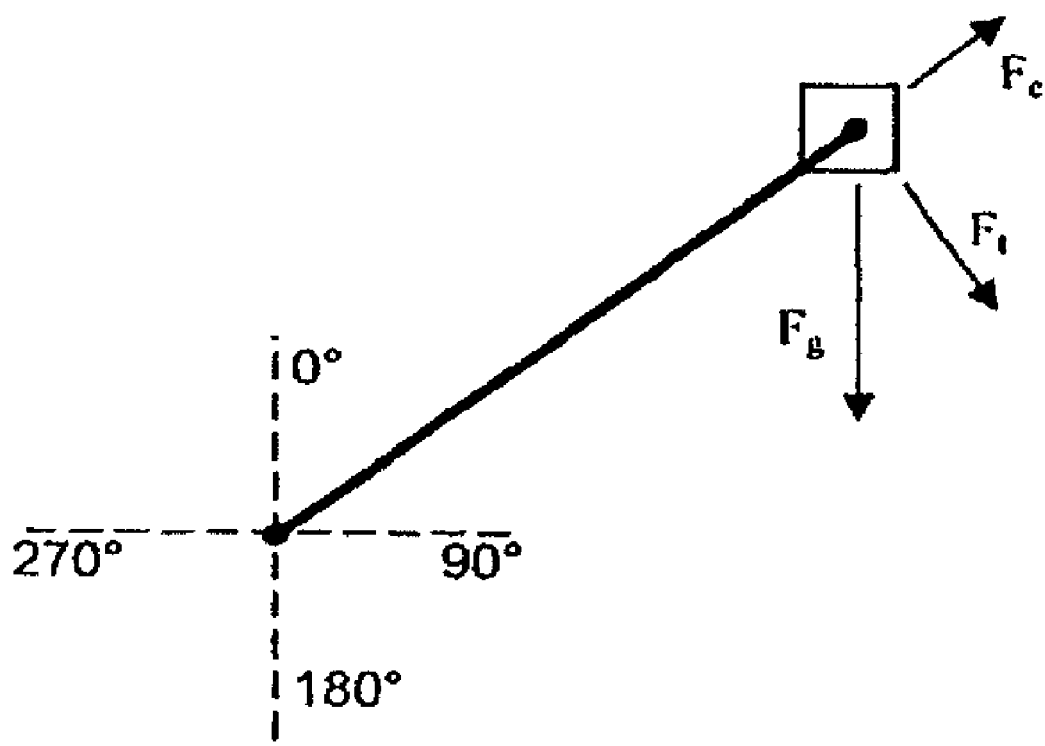
FIG. 11 illustrates the centrifugal force $F_c$ and gravitational force $F_g$ combining to produce total force $F_t$ at the end of the crank.

It was found that the accelerometer 14 should be mounted as close as possible to the axle of the pedal 2, to provide accurate measurement of acceleration forces at the end of the crank 3 without introducing a requirement to compensate in the mathematical processing for a physical offset from the end of the crank. As the crank 3 rotates, the accelerometer 14 attached to cleat 11 will register the centrifugal force $F_c$ generated by the rotation, as shown in FIG. 11. The direction of the centrifugal force on the accelerometer will always be away from the centre of rotation of the crank, so that as the shoe/cleat assembly containing the accelerometer 14 moves around at the end of the crank the direction of the centrifugal force acting on the accelerometer will rotate. Gravity is a constant acceleration acting vertically downwards, and it affects the force that is measured by the accelerometer. The total force $F_t$ measured by the accelerometer will be the combination of gravitational force $F_g$ (constant in direction and magnitude) and centrifugal force $F_c$ (its direction rotates, and its magnitude varies as cadence varies).

Figure 12:
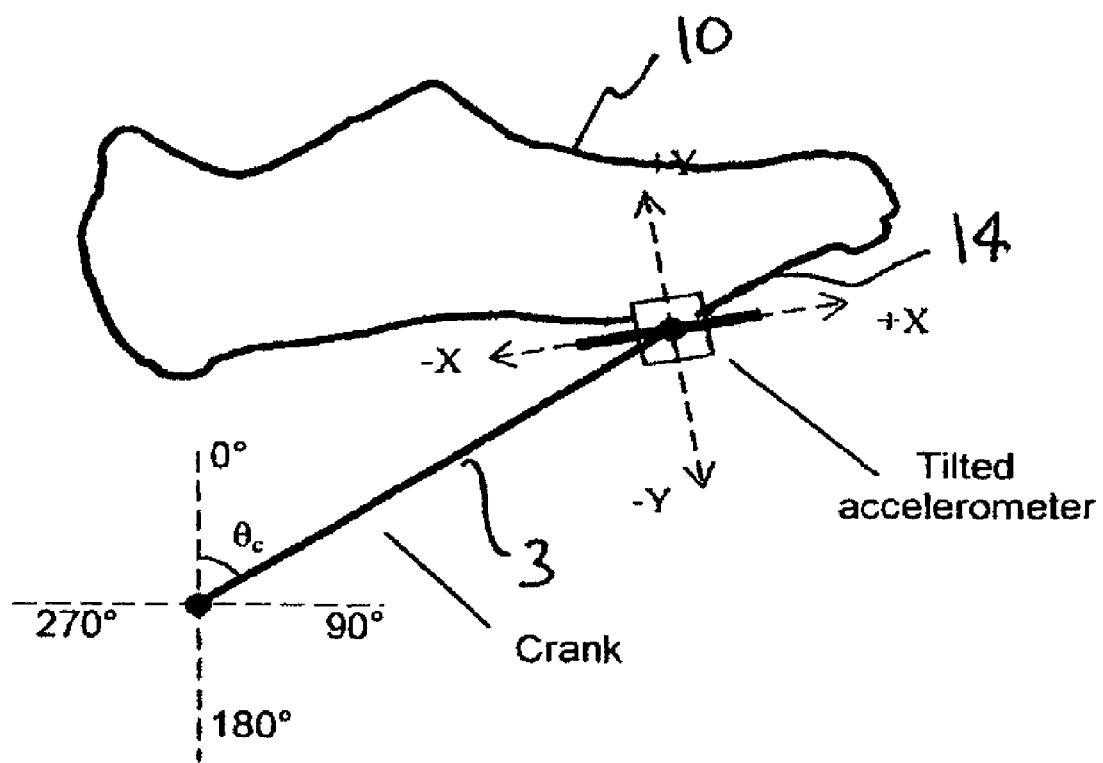
FIG. 12 illustrates the effect of a non-horizontal foot position causing tilting of the accelerometer axes.

In practice, a typical cyclist does not hold their foot horizontal, or at any fixed angle, as they pedal. It rocks back and forth around the horizontal by a small amount, a movement known as "ankling". As the accelerometer 14 is attached to the cyclist's shoe or cleat, the X and Y axes of the accelerometer will also rock back and forth slightly around the horizontal, as illustrated in FIG. 12. This means that the axes of the accelerometer have some unknown changing relationship to the horizontal. However, by making use of the effect of gravity on the accelerometer 14 the present invention can determine the top and bottom of the crank revolution accurately.

Figure 13:
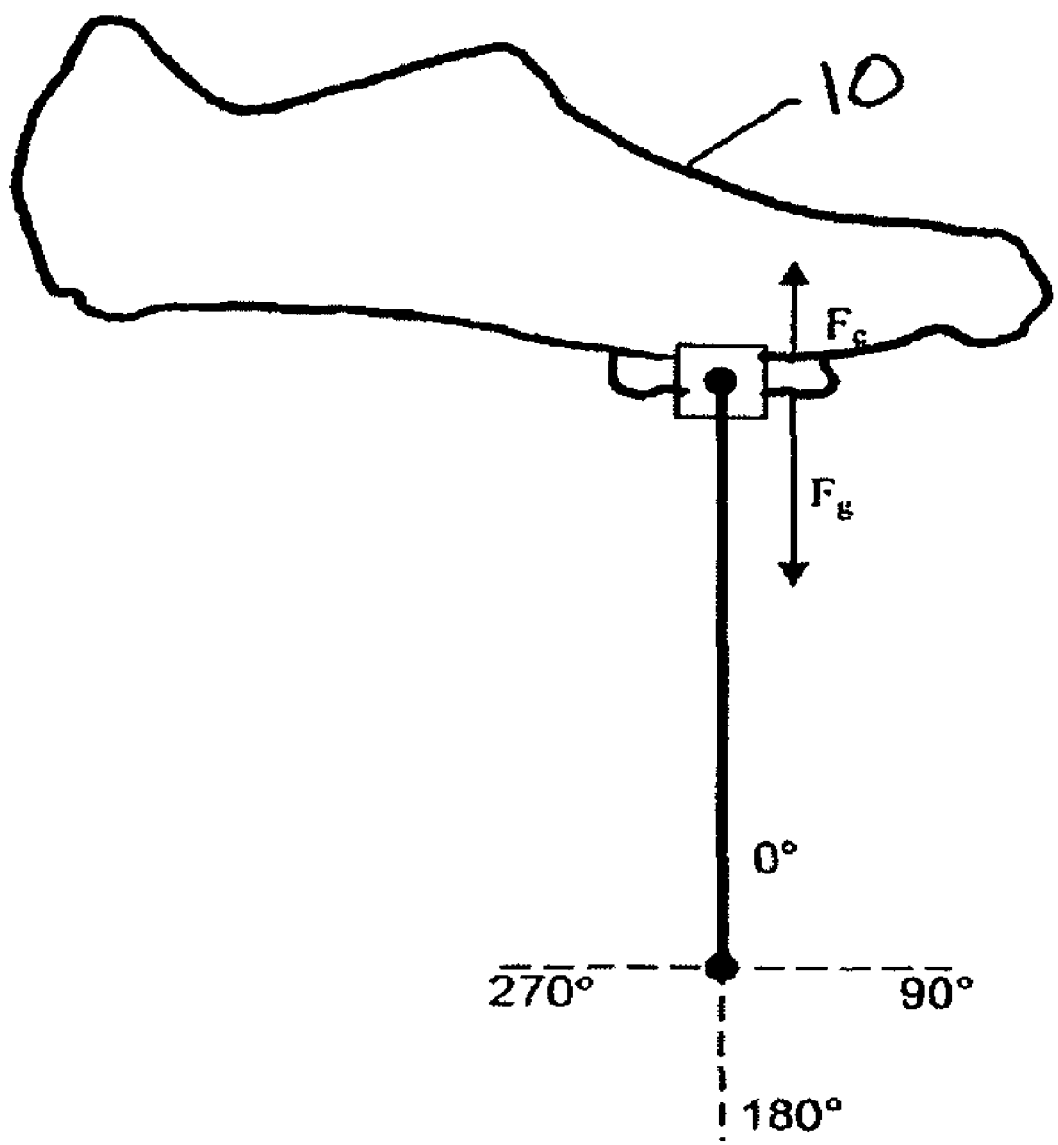
FIG. 13 illustrates the effect of gravity on the total force $F_t$ at the top of the crank revolution.
Figure 14:
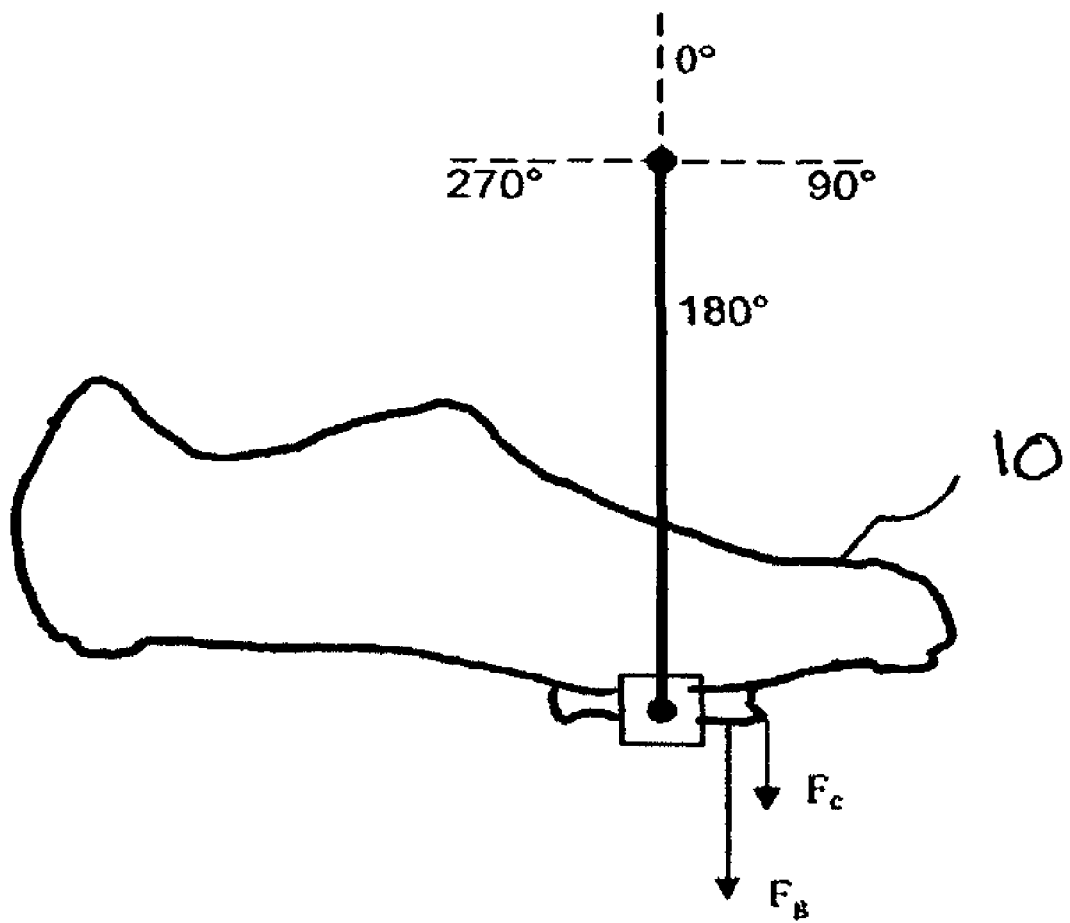
FIG. 14 illustrates the effect of gravity on the total force $F_t$ at the bottom of the crank revolution.

The top and the bottom of the crank revolution is calculated by noting that when the crank is at the top of its revolution the acceleration due to centrifugal force and the acceleration due to gravity are in opposite directions, so the magnitude of the acceleration measured at the end of the crank 3 is the difference between them, $F_c-F_g$, as illustrated in FIG. 13. Conversely, when the accelerometer 14 is at the bottom of the crank revolution the centrifugal acceleration and gravity's acceleration are both downwards, so the magnitude of the measured acceleration is the sum of the two of them, $F_c+F_g$, as illustrated in FIG. 14. Thus, the magnitude of the measured acceleration will be a minimum at the top of the revolution and a maximum at the bottom. The invention found that finding the minimum and the maximum magnitude in a series of acceleration measurements allows accurate identification of the top dead centre (TDC) and bottom dead centre (BDC) of the revolution independently of the orientation of the accelerometer 14 with respect to the horizontal. This provides two absolute reference points for the angular position of the crank.

The absolute angular position of the crank 3 at all measurement points between these two reference points is determined by using time. By making the reasonable assumption of a constant rate of rotation between the reference points at TDC and BDC, and by using the elapsed time from the most recent TDC or BDC the angular position of the crank 3 at a specified time can be calculated.

In another important aspect of the present invention it is possible to derive the cleat and pedal angle using accelerometer measurements, as described in Step 6 of the algorithm mentioned below. In order to calculate torque and power it is necessary to know either $F_v$ the vertical component of the force, or $F_{eff}$ the component perpendicular to the crank, as already illustrated in FIGS. 4 and 5. To calculate $F_v$ or $F_{eff}$ requires the magnitude and angle of the force $F_{app}$ applied by the cyclist at the time of each sample, and the angle must be with respect to the position of the crank at the time of the sample.

The magnitude of $F_{app}$ and the direction of $F_{app}$ with respect to the axes of the accelerometer 14 can be calculated from the normal force $F_N$ and the shear force $F_S$ measured by the embedded force sensors 13. In order to calculate the direction of $F_{app}$ with respect to the crank 3 it is necessary to know the angle of the accelerometer axes with respect to the crank at the time of the sample.

Figure 15:
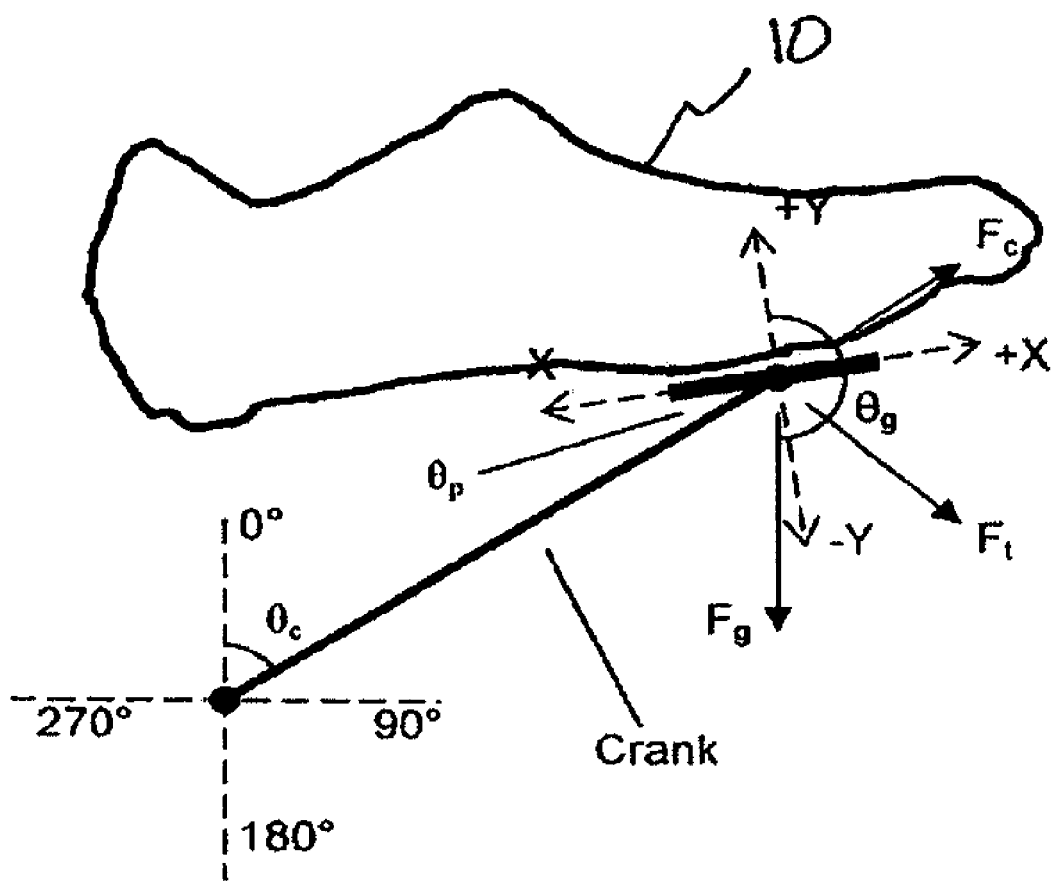
FIG. 15 illustrates the relationship between the axes of the accelerometer, the force $F_t$ resulting from $F_c$ and $F_g$, and the calculated angles $\theta_g$ between gravity and the accelerometer axis and $\theta_p$ between the pedal and the crank.

This can be calculated using the measurements from the accelerometer 14, which is attached to the cleat and shoe assembly. The total force $F_t$ acting on the accelerometer 14 is a combination of centrifugal force $F_c$ and gravitational force $F_g$. The direction and magnitude of $F_t$ is provided by the values from the accelerometer, the magnitude of $F_c$ can be calculated using the cadence and the length of the crank, and the magnitude of $F_g$ is a known constant whose variations due to location and altitude are negligible for these calculations. This allows calculation of the direction of both $F_c$ and $F_g$ with respect to the axes of the accelerometer. As the direction of $F_c$ is directly outwards from the line of the crank, and the direction of $F_g$ is always vertically downwards, this allows calculation of the angle $\theta_p$ between the crank and the plane of the cleat and pedal, as illustrated in FIG. 15. It also gives the angle of tilt of the cyclist's shoe and foot forwards or backwards from the true horizontal at the instant of the sample.

Figure 16:
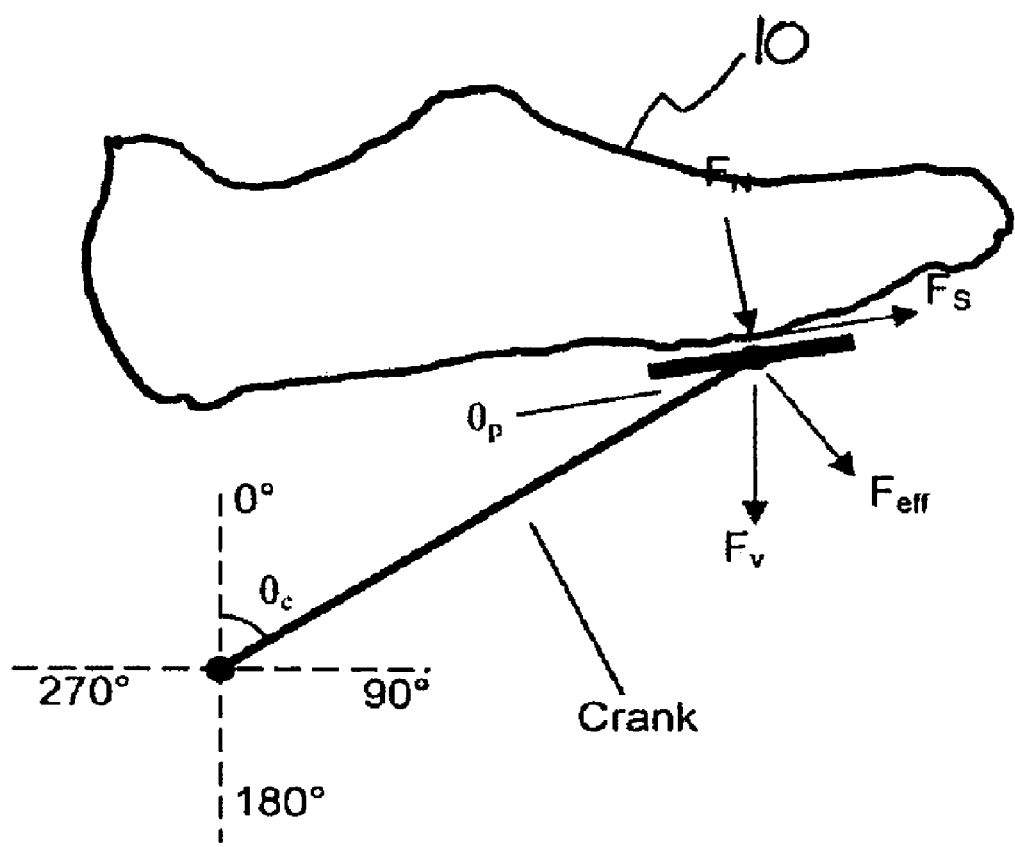
FIG. 16 illustrates the relationships between the measured forces $F_N$ and $F_S$ resulting from applied force $F_{app}$, the angle $\theta_p$ between pedal and crank, the rotational position $\theta_c$ of the crank, and the calculated force components $F_v$ and $F_{eff}$.

In order to calculate torque and power the crank angle $\theta_c$, the pedal to crank angle $\theta_p$, and the magnitudes of the normal and shear forces $F_N$ and $F_S$ allow calculation of both $F_v$ the vertical component of the applied force, and $F_{eff}$ the effective component perpendicular to the crank, as illustrated in FIG. 16. Either of these forces can be used to calculate the torque at the crank 3, and by combining this with the speed of crank rotation, the power may be calculated.

It will be appreciated that the above measurements can be implemented using an algorithm for calculating the values of cadence, torque and power at the time of any sample. Each sample includes the following measurements for each crank:

$F_X$ and $F_Y$, the components of the force due to acceleration along the X and Y axes of the accelerometer, representing the combined acceleration forces $F_c$ and $F_g$.

$F_N$ and $F_S$, the normal and shear forces in the plane of the pedal and cleat, representing the applied force $F_{app}$. $F_N$ may be positive (compression) or negative (tension).

These can be used to calculate cadence, torque and power separately for each of the left and right cranks. The calculations for the left and right crank will produce the same value for cadence, but may produce different values for torque and power depending on the power balance between the left and right feet of the cyclist. The total torque and total power output of the cyclist at any instant is the sum of the torque and the sum of the power from the left and right sides.

An example algorithm to implement the present invention for using $F_X$, $F_Y$, $F_N$ and $F_S$ to calculate cadence, torque and power at the instant of any sample is as follows:

1. $F_X$ and $F_Y$ allow calculation of the angle and magnitude of the total force $F_t$ acting at the end of the rotating crank at the time of the sample. The angle of $F_t$ is with respect to the axes of the accelerometer. $F_t$ is the result of centrifugal force $F_c$ and gravitational force $F_g$.
2. In a set of samples taken during one revolution of the cranks the minimum magnitude of $F_t$ identifies the top dead centre (TDC) of the revolution, and the maximum magnitude of $F_t$ identifies the bottom dead centre (BDC). TDC and BDC are relative to the true vertical (defined by gravity).
3. The time between the most recent TDC and BDC points allows calculation of the speed of crank rotation S (the cadence).
4. For any sample, the cadence and the time since the most recent TDC or BDC allows calculation of the angle $\theta_c$ of the crank forward from TDC at the time of the sample.
5. The cadence and the length of the crank allows calculation of the magnitude of the centrifugal force $F_c$ at the time of any sample.
6. Using the magnitude of $F_c$, the magnitude of $F_g$ (a known constant) and the magnitude and angle of $F_t$ allows calculation of the angle of $F_g$ with respect to the axes of the accelerometer. This gives the angle $\theta_a$ between true vertical and the plane of the pedal and cleat at the time of the sample.
7. Using $\theta_c$ and $\theta_a$ allows calculation of the angle $\theta_p$ between the crank and the pedal at the time of the sample.
8. Using $\theta_p$ and the normal and shear forces $F_N$ and $F_S$ measured by the sensors allows calculation of the effective force $F_{eff}$ perpendicular to the crank and vertical force $F_v$ at the time of the sample. $F_N$ and $F_S$ are derived from the multiple force sensors in the cleat and must be multiplied by calibration constants before use.
9. The torque T at the time of the sample is calculated from $F_{eff}$ and the length L of the crank. Alternatively, the torque T can be calculated from the vertical force $F_v$, the crank angle $\theta_c$ and the length L of the crank.
10. The power P at the time of the sample is calculated from the torque T and the cadence S.

The display and control unit 16 receives the data at regular intervals from both left and right cleats, and continuously processes the data to produce figures for torque and power output, power balance between left and right feet, and cadence. The unit 16 displays these figures to the cyclist, as they are of immediate interest during training and competition. The unit 16 records the figures at regular intervals for later analysis.

The unit 16 can also record other information for later analysis. Specifically, it can record the values measured from each force sensor and from each accelerometer at various points on each revolution of the cranks. This allows detailed analysis of pedalling style by examining how the cyclist applies force to the pedals, including variation in total applied force as the cranks rotate, variation in the side-to-side forces from each foot, and variations in the front-to-back angle of each foot. This information can help a cyclist identify areas where improvements in pedalling efficiency can be achieved.

The system can be used with an enhanced display and control unit 16 intended for use in a laboratory or static test environment. The enhanced unit supports display and real-time analysis of all of the values being measured by the system. This is designed for use by coaches and trainers to observe a cyclist in action so that they can provide feedback on possible improvements to pedalling technique.

The system may be integrated with other measurement and monitoring systems, to include quantities such as speed, heart rate, air temperature, altitude and geographical location.

It will be appreciated that the techniques described above can be applied for measuring force and repetitive movements in shoes in other sports, such as running, rowing and skiing. In addition the techniques disclosed by the present invention can be applied for rehabilitation and physiotherapy on static and mobile bicycles or with static bicycles in a laboratory for research.

The embodiments in the invention described with reference to the drawings comprise a computer apparatus and/or processes performed in a computer apparatus. However, the invention also extends to computer programs, particularly computer programs stored on or in a carrier adapted to bring the invention into practice. The program may be in the form of source code, object code, or a code intermediate source and object code, such as in partially compiled form or in any other form suitable for use in the implementation of the method according to the invention. The carrier may comprise a storage medium such as ROM, e.g. CD ROM, or magnetic recording medium, e.g. a floppy disk or hard disk. The carrier may be an electrical or optical signal which may be transmitted via an electrical or an optical cable or by radio or other means.

The invention is not limited to the embodiments hereinbefore described but may be varied in both construction and detail.

The invention claimed is:

1. A measurement device for measuring a cyclist's power output, in response to an external force provided by said cyclist applied to a bicycle, comprising a force sensor embedded in a bicycle cleat and configured to measure the power output of the cyclist based on the external force provided by said cyclist.

2. The measurement device of claim 1 further comprising an accelerometer.

3. The measurement device of claim 1 wherein said embedded force sensor comprises a first sensor substantially positioned near the inner edge of said cleat and a second sensor substantially positioned near the outer edge of said cleat.

4. The measurement device of claim 1 wherein said embedded force sensor comprises a first sensor substantially positioned near the inner edge of said cleat and a second sensor substantially positioned near the outer edge of said cleat, wherein the embedded force sensor comprises a third sensor substantially positioned near the centre of said cleat.

5. The measurement device of claim 1 wherein said force sensor comprises means for measuring the compression force applied to said cleat.

6. The measurement device of claim 1 wherein said force sensor comprises means for measuring the shear force applied to said cleat.

7. The measurement device of claim 1 wherein a separate force sensor embedded in said cleat comprises means for measuring the tension on the cleat when said cleat is being pulled upwards, in response to a force provided by said cyclist.

8. The measurement device of claim 1 further comprising an accelerometer, wherein said accelerometer comprises means to measure pedalling cadence.

9. The measurement device of claim 1 further comprising an accelerometer wherein said accelerometer comprises means to detect the true top of a crank revolution.

10. The measurement device of claim 1 further comprising an accelerometer wherein said accelerometer comprises means to detect the true bottom of a crank revolution.

11. The measurement device of claim 1 further comprising an accelerometer wherein said accelerometer comprises means to measure the angular position of the crank.

12. The measurement device of claim 1 further comprising an accelerometer wherein said accelerometer comprises means to measure forward/backward tilt of the pedal.

13. A bicycle cleat comprising the measurement device of claim 1.

14. A measurement device for measuring a cyclist's power output, in response to an external force provided by said cyclist applied to a bicycle pedal, comprising an accelerometer, said accelerometer comprises means for measuring cadence and crank position and pedal tilt.

15. A bicycle cleat comprising the measurement device of claim 14.

16. A method of measuring a cyclist's power output, in response to an external force provided by said cyclist applied to a bicycle, comprising the step of using a force sensor embedded in a bicycle cleat to measure the power output of the cyclist based on the external force applied to the bicycle by said cyclist.

17. The method of claim 16 comprising the additional step of using an accelerometer.

* * * * *